US012668762B1

(12) United States Patent
Alvey et al.

(10) Patent No.: US 12,668,762 B1
(45) Date of Patent: Jun. 30, 2026

(54) PROCESSES AND SYSTEMS USING A MODULAR MULTI-STAGE ANAEROBIC DIGESTER

(71) Applicant: Swinergy, Inc., Minneapolis, MN (US)

(72) Inventors: Eugene Alvey, Bloomington, MN (US); Shane Farnell, Prior Lake, MN (US); Amy Crary, Fridley, MN (US)

(73) Assignee: Swinergy, Inc., Minneapolis, MN (US)

( * ) Notice: Subject to any disclaimer, the term of this patent is extended or adjusted under 35 U.S.C. 154(b) by 0 days.

(21) Appl. No.: 19/405,617

(22) Filed: Dec. 2, 2025

Related U.S. Application Data

(60) Provisional application No. 63/846,253, filed on Jul. 18, 2025.

(51) Int. Cl.
    *C12M 1/107*     (2006.01)
    *C12M 1/34*     (2006.01)

(52) U.S. Cl.
    CPC ............ *C12M 21/04* (2013.01); *C12M 41/34* (2013.01)

(58) Field of Classification Search
    None
    See application file for complete search history.

(56) References Cited

U.S. PATENT DOCUMENTS

| | | | | |
|---|---|---|---|---|
| 2008/0124775 A1* | 5/2008 | Kovacs | .................. | C12P 5/023 |
| | | | | 435/167 |
| 2013/0236952 A1* | 9/2013 | Hazewinkel | ............ | C05F 17/50 |
| | | | | 435/287.1 |
| 2020/0339458 A1* | 10/2020 | Aggarwal | ............... | C02F 3/348 |

FOREIGN PATENT DOCUMENTS

| | | | | | |
|---|---|---|---|---|---|
| CN | 118684401 A | * | 9/2024 | | |
| DE | 102011008186 A1 | * | 7/2012 | ............... | C12N 1/20 |
| WO | WO-2013156784 A1 | * | 10/2013 | ............. | C02F 3/284 |
| WO | WO-2015037989 A1 | * | 3/2015 | ............. | C02F 3/006 |
| WO | WO-2024156988 A1 | * | 8/2024 | ........... | C12M 23/34 |

OTHER PUBLICATIONS

University of Maryland, "Anaerobic Digestion: Basic Processes for Biogas Production", Fact Sheet FS-994 Oct. 2014, pp. 1-7. (Year: 2014).*

* cited by examiner

*Primary Examiner* — William H. Beisner
(74) *Attorney, Agent, or Firm* — O'Connor & Company; Ryan P. O'Connor

(57) ABSTRACT

Some variations provide a multi-stage process for anaerobic digestion of animal manure, comprising: providing a feedstock comprising animal manure; introducing feedstock with a hydrolytic microorganism to a hydrolysis stage; introducing feedstock with an acidogenic microorganism to an acidogenesis stage; introducing feedstock with a methanogenic microorganism to a methanogenesis stage; forming an anaerobic environment in each stage; monitoring the gas composition and the ratio of volatile fatty acids to total alkalinity in each of the hydrolysis stage, the acidogenesis stage, and the methanogenesis stage; and feeding a steady-state amount of the feedstock into the hydrolysis stage, and processing the steady-state amount of the feedstock, continuously or intermittently, through the hydrolysis stage, the acidogenesis stage, and the methanogenesis stage, thereby generating a product comprising biogas. There are numerous advantages of the disclosed process and system compared to the prior art, including faster processing speed, higher biomethane yield, and lower capital costs.

14 Claims, 5 Drawing Sheets

PROCESSES AND SYSTEMS USING A MODULAR MULTI-STAGE ANAEROBIC DIGESTER

PRIORITY DATA

This non-provisional patent application claims priority to U.S. Patent App. No. 63/846,253, filed on Jul. 18, 2025, which is hereby incorporated by reference.

FIELD

The present invention generally relates to anaerobic digestion of animal manure, such as swine manure, and/or other feedstocks capable of being anaerobically digested.

BACKGROUND

Global livestock produces the equivalent of over 7 gigatons of carbon dioxide annually, posing significant environmental challenges for farmers and their communities. In the United States alone, over 1.4 billion tons of animal manure is generated annually, generating significant greenhouse-gas emissions. In addition to vapor emissions, run-off from animal waste can raise nitrate levels in groundwater. There is a need to provide a solution to reduce the environmental impact of animal waste while providing clean, affordable energy to local communities.

Anaerobic digestion is a series of biological processes in which microorganisms break down biodegradable material in the absence of oxygen. One of the end products is biogas, which may be combusted to generate electricity and heat, or processed into renewable natural gas, transportation fuels, or chemicals. Known anaerobic digestion technologies can convert livestock manure, municipal wastewater solids, food waste, industrial wastewater residuals, fats, oils, grease, and various other organic waste streams into biogas.

The conventional digestion process begins with bacterial hydrolysis of the input materials in order to break down organic polymers such as carbohydrates and make them available for other bacteria. Acidogenic bacteria convert the sugars and amino acids into carbon dioxide, hydrogen, ammonia, and organic acids. Acetogenic bacteria convert the organic acids into acetic acid, along with additional ammonia, hydrogen, and carbon dioxide. Finally, methanogens convert these products to methane and carbon dioxide.

In the field of anaerobic digestion of animal manure, conventional technology separates the process into particular stages or optimizes the environment of an anaerobic digester to improve performance, such as to reduce process time, improve energy efficiency, or increase biogas yields. Zhang et al., "Three-stage anaerobic co-digestion of food waste and horse manure", *Scientific Reports* 7:1269 (Apr. 28, 2017) is hereby incorporated by reference. Known problems with anaerobic digestion involve long processing times and insufficient production of biomethane from a feedstock. These challenges in the marketplace result in extremely low market penetration (less than 4% on commercial livestock farms), which is due to high capital costs, large infrastructure footprints, and bespoke designs required for each digester site. From a biochemical perspective, these challenges are the result of sub-optimal environmental conditions for the various microorganisms involved.

Improved anaerobic digestion processes are needed-especially practical and scalable processes to rapidly transform farm waste into renewable natural gas.

SUMMARY

Some variations of the invention provide a multi-stage process for anaerobic digestion of animal manure, wherein the multi-stage process comprises:

(a) providing a feedstock comprising animal manure, wherein the animal manure is in liquid form dissolved in water and/or slurry form suspended in water;

(b) introducing a first start-up amount of the feedstock and a hydrolytic microorganism to a hydrolysis stage, wherein the first start-up amount of the feedstock and the hydrolytic microorganism are introduced batch-wise, and wherein the hydrolytic microorganism is contained with the first start-up amount of said feedstock, is separately added to the hydrolysis stage, or a combination thereof;

(c) introducing a second start-up amount of the feedstock and an acidogenic microorganism to an acidogenesis stage, wherein the second start-up amount of the feedstock and the acidogenic microorganism are introduced batchwise, and wherein the acidogenic microorganism is contained with the second start-up amount of said feedstock, is separately added to the acidogenesis stage, or a combination thereof;

(d) introducing a third start-up amount of the feedstock and a methanogenic microorganism to a methanogenesis stage, wherein the third start-up amount of the feedstock and the methanogenic microorganism are introduced batchwise, and wherein the methanogenic microorganism is contained with the third start-up amount of said feedstock, is separately added to the methanogenesis stage, or a combination thereof;

(e) forming an anaerobic environment in each of the hydrolysis stage, the acidogenesis stage, and the methanogenesis stage;

(f) monitoring the gas composition and the ratio of volatile fatty acids to total alkalinity in each of the hydrolysis stage, the acidogenesis stage, and the methanogenesis stage; and (g) feeding a steady-state amount of the feedstock into the hydrolysis stage, and processing the steady-state amount of the feedstock, continuously or intermittently, through the hydrolysis stage, the acidogenesis stage, and the methanogenesis stage, thereby generating a product comprising biogas.

In some embodiments, the animal manure is swine manure.

In some embodiments, step (g) is triggered based on monitored gas composition obtained during step (f). In some embodiments, step (g) is triggered based on monitored ratio of volatile fatty acids to total alkalinity obtained during step (f). In certain embodiments, step (g) is triggered based on both monitored gas composition obtained during step (f), and monitored ratio of volatile fatty acids to total alkalinity obtained during step (f).

In some embodiments, the hydrolytic microorganism has a genus selected from the group consisting of *Coprothermobacter, Acetomicrobium*, and *Thermoanaerobacterium*.

In some embodiments, the hydrolysis stage is operated in step (g) at a hydrolysis temperature selected from about 50° C. to about 65° C.

In some embodiments, the hydrolysis stage is operated in step (g) at a hydrolysis-stage residence time selected from about 1 day to about 5 days.

In some embodiments, the acidogenic microorganism has a genus selected from the group consisting of *Acetitomaculum, Acetoanaerobium, Acetonema, Anaerovorax*, Candidatus Phosphitivorax, Dehalobacterium, *Moorella*, Romboutsia, *Ruminococcus*, and Terrisporobacter.

In some embodiments, the acidogenesis stage is operated in step (g) at an acidogenesis temperature selected from about 50° C. to about 70° C.

In some embodiments, the acidogenesis stage is operated in step (g) at an acidogenesis-stage residence time selected from about 5 days to about 14 days.

In some embodiments, the methanogenic microorganism has a genus selected from the group consisting of *Methanobacterium, Methanoculleus, Methanothermobacter, Methanosarcina, Methanothrix,* and *Methanospirillum.*

In some embodiments, the methanogenesis stage is operated in step (g) at a methanogenesis temperature selected from about 50° C. to about 75° C.

In some embodiments, the methanogenesis stage is operated in step (g) at a methanogenesis-stage residence time selected from about 7 days to about 14 days.

In some embodiments, the total residence time is about 30 days or less, wherein the total residence time is defined as the sum of the hydrolysis-stage residence time, the acidogenesis-stage residence time, and the methanogenesis-stage residence time. In certain embodiments, the total residence time is about 15 days or less.

In some embodiments, step (f) includes monitoring concentration of $H_2S$ to indicate a transition from hydrolysis to acidogenesis.

In some embodiments, the biogas produced in step (g) has a biomethane yield of at least 80%, wherein the biomethane yield is calculated as the ratio, expressed as a percentage, of the biomethane in the product divided by total biomethane potential associated with the feedstock. In certain embodiments, the biomethane yield is at least 85% or at least 90%.

Other variations provide a multi-stage anaerobic digester for anaerobic digestion of animal manure, wherein the multi-stage anaerobic digester comprises:

a digester input;

a hydrolysis stage connected to the digester input;

an acidogenesis stage connected to the hydrolysis stage, wherein the acidogenesis stage is physically separate from the hydrolysis stage;

a methanogenesis stage connected to the acidogenesis stage, wherein the methanogenesis stage is physically separate from the acidogenesis stage; and a digester output configured to recover a product comprising biogas, wherein each of the hydrolysis stage, the acidogenesis stage, and the methanogenesis stage is capable of forming an anaerobic environment, and wherein each of the hydrolysis stage, the acidogenesis stage, and the methanogenesis stage is configured with a first monitor and a second monitor, wherein the first monitor is configured for monitoring the gas composition, and wherein the second monitor is configured for monitoring the ratio of volatile fatty acids to total alkalinity.

In some embodiments, the multi-stage anaerobic digester is modular. Modules may be delivered to a processing facility site for simple installation. The processing speed and automation, high biomethane yields, and system modularity results in a scalable technology capable of penetrating the entire hog and dairy commercial farming industries.

In some embodiments, the first monitor is configured for monitoring concentration of $H_2S$ to indicate a transition from hydrolysis to acidogenesis.

In some embodiments, the multi-stage anaerobic digester utilizes a single pump.

In typical embodiments, the digester output is connected to one or more biogas bladders.

In some embodiments, the multi-stage anaerobic digester is configured to achieve a total residence time of about 30 days or less, such as about 15 days or less.

In some embodiments, the digester input is configured to receive a feedstock comprising animal manure (e.g., swine manure) in liquid form dissolved in water and/or slurry form suspended in water. The digester input may be configured to receive a feedstock comprising solid biomass and/or liquid biomass, with or without manure present in the feedstock.

During operation, the animal manure is contained within the multi-stage anaerobic digester. Prior to operation, or when the multi-stage anaerobic digester is shut down, there is no animal manure contained within the anaerobic digester.

DETAILED DESCRIPTION OF EMBODIMENTS

Figure 1:
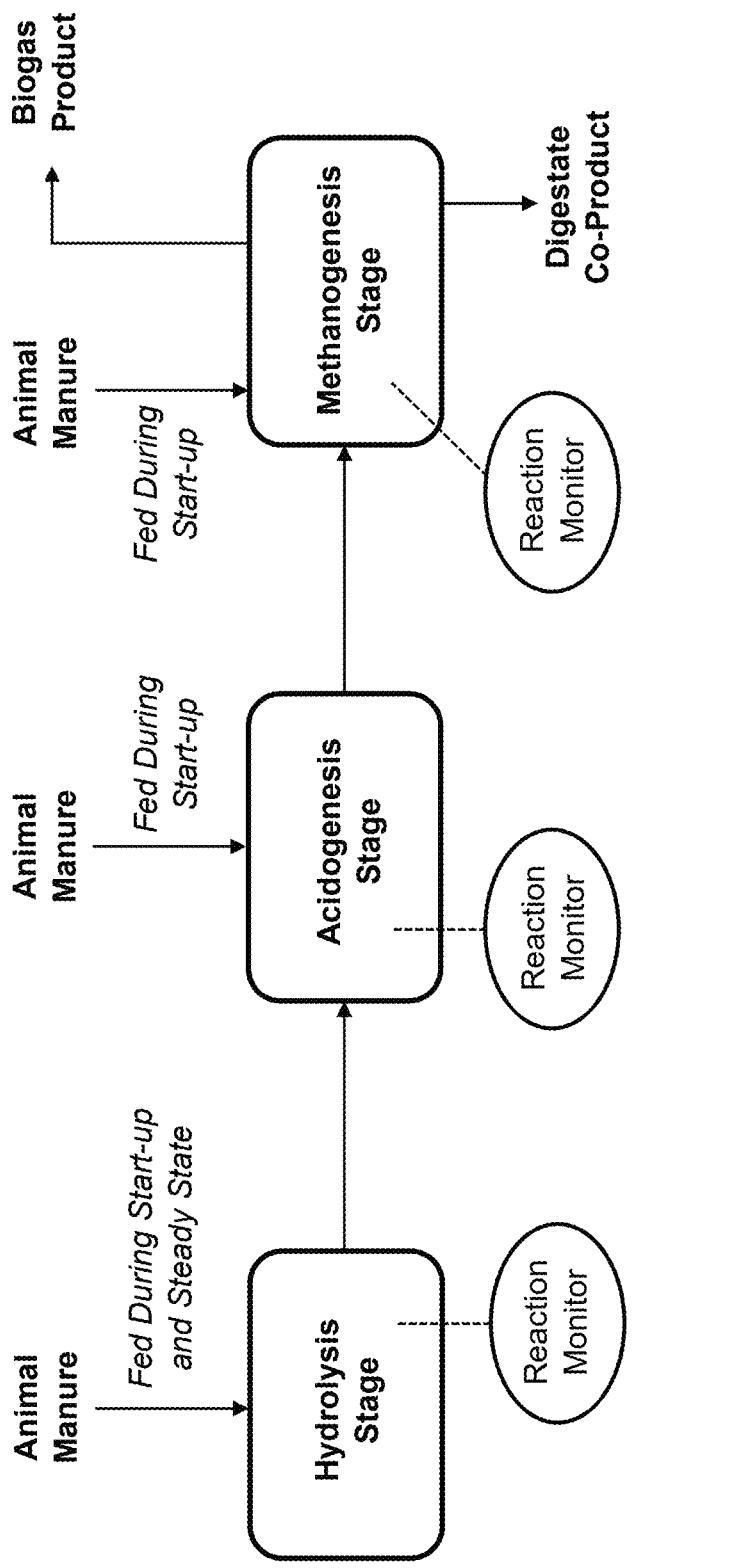
FIG. 1 is an exemplary block-flow process diagram of a multi-stage process for anaerobic digestion of animal manure.

The processes and systems of the present invention will be described in detail by reference to various non-limiting embodiments.

This description will enable one skilled in the art to make and use the invention, and it describes several embodiments, adaptations, variations, alternatives, and uses of the invention. These and other embodiments, features, and advantages of the present invention will become more apparent to those skilled in the art when taken with reference to the following detailed description of the invention in conjunction with the accompanying drawings.

As used in this specification and the appended claims, the singular forms "a," "an," and "the" include plural referents unless the context clearly indicates otherwise. Unless defined otherwise, all technical and scientific terms used herein have the same meaning as is commonly understood by one of ordinary skill in the art to which this invention belongs.

Unless otherwise indicated, all numbers expressing conditions, concentrations, dimensions, and so forth used in the specification and claims are to be understood as being modified in all instances by the term "about." Accordingly, unless indicated to the contrary, the numerical parameters set forth in the following specification and attached claims are approximations that may vary depending at least upon a specific analytical technique.

The term "comprising," which is synonymous with "including," "containing," or "characterized by" is inclusive or open-ended and does not exclude additional, unrecited elements or method steps. "Comprising" is a term of art used in claim language which means that the named claim elements are essential, but other claim elements may be added and still form a construct within the scope of the claim.

As used herein, the phrase "consisting of" excludes any element, step, or ingredient not specified in the claim. When the phrase "consists of" (or variations thereof) appears in a clause of the body of a claim, rather than immediately following the preamble, it limits only the element set forth in that clause; other elements are not excluded from the claim as a whole. As used herein, the phrase "consisting essentially of" limits the scope of a claim to the specified elements or method steps, plus those that do not materially affect the basis and novel characteristic(s) of the claimed subject matter.

With respect to the terms "comprising," "consisting of," and "consisting essentially of," where one of these three terms is used herein, the presently disclosed and claimed subject matter may include the use of either of the other two terms, except in the case of a Markush group. Thus in some embodiments not otherwise explicitly recited, any instance of "comprising" may be replaced by "consisting of" or, alternatively, by "consisting essentially of."

The presently disclosed technology is designed to solve one of the greatest environmental problems today. Traditional anaerobic digestion is improved by providing a scalable multi-stage digestion system that can process liquid or slurry animal manure in a fraction of the time and with significantly higher biomethane yield, compared to conventional digestion systems. Some embodiments utilize heretofore-unknown procedures for start-up and curation of stages, leading to higher process efficiency at steady state.

Some variations of the invention provide a multi-stage process for anaerobic digestion of animal manure, wherein the multi-stage process comprises:

(a) providing a feedstock comprising animal manure, wherein the animal manure is in liquid form dissolved in water and/or slurry form suspended in water;

(b) introducing a first start-up amount of the feedstock and a hydrolytic microorganism to a hydrolysis stage, wherein the first start-up amount of the feedstock and the hydrolytic microorganism are introduced batchwise, and wherein the hydrolytic microorganism is contained with the first start-up amount of said feedstock, is separately added to the hydrolysis stage, or a combination thereof;

(c) introducing a second start-up amount of the feedstock and an acidogenic microorganism to an acidogenesis stage, wherein the second start-up amount of the feedstock and the acidogenic microorganism are introduced batchwise, and wherein the acidogenic microorganism is contained with the second start-up amount of said feedstock, is separately added to the acidogenesis stage, or a combination thereof;

(d) introducing a third start-up amount of the feedstock and a methanogenic microorganism to a methanogenesis stage, wherein the third start-up amount of the feedstock and the methanogenic microorganism are introduced batchwise, and wherein the methanogenic microorganism is contained with the third start-up amount of said feedstock, is separately added to the methanogenesis stage, or a combination thereof;

(e) forming an anaerobic environment in each of the hydrolysis stage, the acidogenesis stage, and the methanogenesis stage;

(f) monitoring the gas composition and the ratio of volatile fatty acids to total alkalinity in each of the hydrolysis stage, the acidogenesis stage, and the methanogenesis stage; and (g) feeding a steady-state amount of the feedstock into the hydrolysis stage, and processing the steady-state amount of the feedstock, continuously or intermittently, through the hydrolysis stage, the acidogenesis stage, and the methanogenesis stage, thereby generating a product comprising biogas.

In some embodiments, the animal manure is swine manure. The invention is by no means limited to processing of swine manure. Other types of animal manure that may be processed according to the principles taught herein include, but are not limited to, cow manure, sheep manure, horse manure, goat manure, chicken manure, turkey manure, or mixtures thereof. The feedstock may be a mixture of animal manure and solid biomass (e.g., straw). In certain variations, the feedstock does not contain any animal manure but rather contains solid and/or liquid biomass. In certain embodiments, the feedstock includes palm oils or waste fish components (e.g., fish innards).

Some variations thus provide a multi-stage process for anaerobic digestion of biomass, wherein the multi-stage process comprises:

(a) providing a feedstock comprising biomass and water;

(b) introducing a first start-up amount of the feedstock and a hydrolytic microorganism to a hydrolysis stage, wherein the first start-up amount of the feedstock and the hydrolytic microorganism are introduced batchwise, and wherein the hydrolytic microorganism is contained with the first start-up amount of said feedstock, is separately added to the hydrolysis stage, or a combination thereof;

(c) introducing a second start-up amount of the feedstock and an acidogenic microorganism to an acidogenesis stage, wherein the second start-up amount of the feedstock and the acidogenic microorganism are introduced batchwise, and wherein the acidogenic microorganism is contained with the second start-up amount of said feedstock, is separately added to the acidogenesis stage, or a combination thereof;

(d) introducing a third start-up amount of the feedstock and a methanogenic microorganism to a methanogenesis stage, wherein the third start-up amount of the feedstock and the methanogenic microorganism are introduced batchwise, and wherein the methanogenic microorganism is contained with the third start-up amount of said feedstock, is separately added to the methanogenesis stage, or a combination thereof;

(e) forming an anaerobic environment in each of the hydrolysis stage, the acidogenesis stage, and the methanogenesis stage;

(f) monitoring the gas composition and the ratio of volatile fatty acids to total alkalinity in each of the hydrolysis stage, the acidogenesis stage, and the methanogenesis stage; and (g) feeding a steady-state amount of the feedstock into the hydrolysis stage, and processing the steady-state amount of the feedstock, continuously or intermittently, through the hydrolysis stage, the acidogenesis stage, and the methanogenesis stage, thereby generating a product comprising biogas.

In some embodiments, step (g) is triggered based on monitored gas composition obtained during step (f). In some embodiments, step (g) is triggered based on monitored ratio of volatile fatty acids to total alkalinity obtained during step (f). In certain embodiments, step (g) is triggered based on both monitored gas composition obtained during step (f), and monitored ratio of volatile fatty acids to total alkalinity obtained during step (f).

The hydrolytic microorganism is preferably selected from bacteria. Mixtures of bacteria may be used for the hydrolytic microorganism. In some embodiments, the hydrolytic microorganism has a genus selected from the group consisting of *Coprothermobacter, Acetomicrobium*, and *Thermoanaerobacterium*. In some embodiments, the hydrolytic microorganism is one or more species selected from the group consisting of *Bacillus smithii, Geobacillus thermodenitrificans, Aneurinibacillus thermoaerophilus, Clostridium thermolacticum*, and *Clostridium thermocellum*. Typically, the hydrolytic microorganism is already contained in the starting feedstock, especially in the case of animal manure. For feedstocks containing or consisting essentially of biomass, it may be necessary or desirable to separately add a hydrolytic microorganism to the hydrolysis stage.

In some embodiments, the hydrolysis stage is operated in step (g) at a hydrolysis temperature selected from about 50° C. to about 65° C. In various embodiments, the hydrolysis temperature is about, at least about, or at most about 50° C., 51° C., 52° C., 53° C., 54° C., 55° C., 56° C., 57° C., 58° C., 59° C., 60° C., 61° C., 62° C., 63° C., 64° C., or 65° C., including any intervening range.

In the context of temperature, an intervening range, such as 55-60° C., can mean that the specific temperature is selected from such sub-range, and/or that the temperature is controlled to be within such sub-range or to intentionally vary over time in the stage.

In some embodiments, the hydrolysis stage is operated in step (g) at a hydrolysis-stage residence time selected from about 1 day to about 5 days. In various embodiments, the hydrolysis-stage residence time is about, at least about, or at most about 1, 2, 3, 4, or 5 days, including any intervening range.

In the context of stage residence time, an intervening range, such as 2-4 days, means that the residence time is selected from such sub-range (e.g., 2 days, 2.5 days, 3.7 days, etc.).

The gas composition exiting the hydrolysis stage is typically about 17.3 vol % $CH_4$, about 78.7 vol % $CO_2$, about 2% $N_2$, and about 1.2 vol % $H_2S$. In various embodiments, the gas composition exiting the hydrolysis stage contains from about 5 vol % to about 25 vol % $CH_4$, from about 50 vol % to about 90 vol % $CO_2$, from about 1 vol % to about 4 vol % $N_2$, and from about 0.1 vol % to about 3 vol % $H_2S$.

The acidogenic microorganism is preferably selected from bacteria of the Clostridia class and Firmicutes phylum. In some embodiments, the acidogenic microorganism has a genus selected from the group consisting of *Acetitomaculum, Acetoanaerobium, Acetonema, Anaerovorax*, Candidatus Phosphitivorax, Dehalobacterium, *Moorella*, Romboutsia, *Ruminococcus*, and Terrisporobacter. In some embodiments, the acidogenic microorganism is one or more species selected from the group consisting of Candidatus Clocimanetes and Actinobacteria. Typically, the acidogenic microorganism is already contained in the starting feedstock, especially in the case of animal manure. For feedstocks containing or consisting essentially of biomass, it may be necessary or desirable to separately add an acidogenic microorganism to the acidogenesis stage.

In some embodiments, the acidogenesis stage is operated in step (g) at an acidogenesis temperature selected from about 50° C. to about 70° C. In various embodiments, the acidogenesis temperature is about, at least about, or at most about 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., or 70° C., including any intervening range.

In some embodiments, the acidogenesis stage is operated in step (g) at an acidogenesis-stage residence time selected from about 5 days to about 14 days. In various embodiments, the acidogenesis-stage residence time is about, at least about, or at most about 5, 6, 7, 8, 9, 10, 11, 12, 13, or 14 days, including any intervening range.

The gas composition exiting the acidogenesis stage is typically about 26.9 vol % $CH_4$, about 70 vol % $CO_2$, about 2% $N_2$, and about 1 vol % $H_2S$. In various embodiments, the gas composition exiting the acidogenesis stage contains from about 10 vol % to about 35 vol % $CH_4$, from about 45 vol % to about 75 vol % $CO_2$, from about 1 vol % to about 3 vol % $N_2$, and from about 0.1 vol % to about 2.5 vol % $H_2S$.

The methanogenic microorganism is preferably selected from archaea of the Euryarchacota, Halobacterota, or Thermoplasmatota phylum; the Methanobacteria or Methanomicrobia class; the Methanobacteriales or Methanosarcinales order; and/or the Methanothermobacteriaceae, Methanotrichaceae, or Methanospirillaceae family. In some embodiments, the methanogenic microorganism has a genus selected from the group consisting of *Methanobacterium, Methanoculleus, Methanothermobacter, Methanosarcina, Methanothrix*, and *Methanospirillum*. In some embodiments, the methanogenic microorganism is one or more species selected from the group consisting of *Methanosarcina thermophila, Methanothrix thermoacetophila*, and *Methanobacterium thermophilum*. Typically, the methanogenic microorganism is already contained in the starting feedstock, especially in the case of animal manure. For feedstocks containing or consisting essentially of biomass, it may be necessary or desirable to separately add a methanogenic microorganism to the methanogenesis stage.

In some embodiments, the methanogenesis stage is operated in step (g) at a methanogenesis temperature selected from about 50° C. to about 75° C. In various embodiments, the methanogenesis temperature is about, at least about, or at most about 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., or 75° C., including any intervening range.

In some embodiments, the methanogenesis stage is operated in step (g) at a methanogenesis-stage residence time selected from about 7 days to about 14 days. In various embodiments, the methanogenesis-stage residence time is about, at least about, or at most about 7, 8, 9, 10, 11, 12, 13, or 14 days, including any intervening range.

In typical embodiments, acetogenesis (formation of acetic acid and/or acetate) is occurring in the methanogenesis stage. There is nearly complete overlap in the ideal environments for acetogenesis and methanogenesis, which is why a distinct acetogenesis stage is not necessary. Methanogenic organisms help maintain a healthy environment for acetogenic organisms; the acetogenic organisms and the methanogenic organisms function synergistically.

The gas composition exiting the methanogenesis stage is typically about 55-65 vol % $CH_4$, about 35-45 vol % $CO_2$, about 2% $N_2$, and less than 1 vol % $H_2S$. In various embodiments, the gas composition exiting the methanogenesis stage contains from about 40 vol % to about 75 vol %

$CH_4$, from about 30 vol % to about 60 vol % $CO_2$, from about 1 vol % to about 3 vol % $N_2$, and from about 0.05 vol % to about 2 vol % $H_2S$.

Steps (b), (c), (d), and (e) may be collectively referred to as an initial feeding sequence. The initial feeding sequence induces various strains of archaea and bacteria which drive a given stage of anaerobic digestion to become dominant in a particular bioreactor or process stage. The three stages of anaerobic digestion which are separately curated are, in sequence, hydrolysis, acidogenesis, and methanogenesis. Across three bioreactors, or bioreactor stages, all three are filled and then an anaerobic environment is developed. Once oxygen is no longer present in the bioreactor, raw feedstock may be progressively fed into the first stage, pumping a corresponding amount of feedstock from each bioreactor (or stage) into the next. In some embodiments, the methanogenesis stage is drained; then, the acidogenesis stage is transferred to the methanogenesis stage; and finally, the hydrolysis stage is filled with fresh feedstock.

The FOS/TAC ratio and gas composition are preferably monitored in each stage to determine when to add fresh feedstock. The FOS/TAC ratio is an acronym of the German terms "Flüchtige Organische Säuren" ("FOC") and Total Alkalischen Carbonaten ("TAC"). In this specification, the FOS/TAC ratio is determined according to Nordmann's FOS/TAC Titration (Nordmann, "Die Überwachung der Schlammfaulung. Eine einfache Methode zur Bestimmung der organischen Säuren und der Kalkreserve im Faulwasser", *Korrespondenz Abwasser, Beilage: KA-Informationen für das Betriebspersonal von Abwasseranlagen* 3, 1977, which is hereby incorporated by reference). The Nordmann titration technique can determine alkalinity and volatile fatty acid (VFA) content of sewage sludge.

The Nordmann titration method was adapted for samples from biogas plants according to McGhee, "A Method For Approximation of the Volatile Acid Concentrations in Anaerobic Digesters", *Water and Sewage Works*, Vol. 115, pp. 162-166, 1968, which is hereby incorporated by reference). The buffering capacity of the system (the value of TAC) is determined by titrating 20 mL samples from their initial pH to pH=5 with sulfuric acid. The TAC is calculated according to EQ. 1:

$$TAC = A \times 250 \qquad \text{EQ. 1}$$

where TAC (mg/L $CaCO_3$) is the total alkalinity, and A (mL) is the equivalent volume of 0.1 N $H_2SO_4$ to reach pH=5. The determination of the VFA concentration (the value of FOS) is based on titration of the solution from pH=5 to pH=4.4. The linear relationship of acid consumption versus FOS then provides EQ. 2:

$$FOS = (B \times 1.66 - 0.15) \times 500 \qquad \text{EQ. 2}$$

where FOS (mg/L HAc) is the VFA content with regards to acetic acid (HAc, $CH_3COOH$), and B (mL) is the equivalent volume difference of 0.1 N $H_2SO_4$ between pH=5 and pH=4.4. The FOS/TAC ratio is then calculated by dividing the measured FOS value by the measured TAC value. Note that EQS. 1 and 2 are based on the titration of a 20 mL sample. The coefficient values in these formulas may vary if a different titration volume is applied.

When gas production starts to taper off and the FOS/TAC ratio is reduced, it is established that microorganisms have substantially processed the feedstock currently in a given bioreactor (stage). This procedure is continued until the FOS/TAC ratio indicates that distinct processing stages have been curated. At this point, three-stage anaerobic digestion is established and high-volume processing takes place at steady state. Once start-up is completed in the three-stage digester, the dominant strains of organisms in each stage are more robust and capable of processing larger volumes of feedstock at an accelerated rate. The system is closely monitored and the ideal living environment for the bacteria—thermophilic temperatures and low oxygen levels—is maintained. Fixed-interval additions of feedstock may then be used, such as with feeding intervals of about 3 to 8 days, up to about 80% (for example) of a bioreactor working volume. In various embodiments, the feeding intervals are about, at least about, or at most about 1, 2, 3, 4, 5, 6, 7, 8, 9, or 10 days, including any intervening range. The fixed-interval additions of feedstock may be used to fill a particular stage to about, at least about, or at most about 50%, 55%, 60%, 65%, 70%, 75%, 80%, 85%, 90%, or 95% by volume.

In step (f), the preferred range of the FOS/TAC ratio is from about 0.3 to about 0.8, and a more-preferred range of the FOS/TAC ratio is from about 0.3 to about 0.5, for each of the hydrolysis stage, the acidogenesis stage, and the methanogenesis stage. A FOS/TAC ratio less than 0.3 indicates that fresh feed needs to be added to the system (typically, via addition to the hydrolysis stage). A FOS/TAC ratio greater than 0.8 indicates that time should elapse before fresh feed should be added to the system.

In various embodiments, the hydrolysis stage is controlled such that the FOS/TAC ratio is about, at least about, or at most about 0.30, 0.31, 0.32, 0.33, 0.34, 0.35, 0.36, 0.37, 0.38, 0.39, 0.40, 0.41, 0.42, 0.43, 0.44, 0.45, 0.46, 0.47, 0.48, 0.49, 0.50, 0.51, 0.52, 0.53, 0.54, 0.55, 0.56, 0.57, 0.58, 0.59, 0.60, 0.61, 0.62, 0.63, 0.64, 0.65, 0.66, 0.67, 0.68, 0.69, 0.70, 0.71, 0.72, 0.73, 0.74, 0.75, 0.76, 0.77, 0.78, 0.79, or 0.80, including any intervening range (e.g., 0.30-0.65).

In the context of the FOS/TAC ratio, an intervening range can refer to a desired range for which the FOS/TAC ratio is controlled and/or a sub-range within which the desired FOS/TAC ratio is selected. Using the example of a FOS/TAC ratio of 0.30-0.65, the stage may be controlled such that the FOS/TAC ratio remains in this range, i.e. does not drop below 0.30 and does not increase beyond 0.65. Alternatively, the stage may be controlled to a set-point FOS/TAC ratio that falls in the 0.30-0.65 range, such as 0.40±0.05.

In various embodiments, the acidogenesis stage is controlled such that the FOS/TAC ratio is about, at least about, or at most about 0.30, 0.31, 0.32, 0.33, 0.34, 0.35, 0.36, 0.37, 0.38, 0.39, 0.40, 0.41, 0.42, 0.43, 0.44, 0.45, 0.46, 0.47, 0.48, 0.49, 0.50, 0.51, 0.52, 0.53, 0.54, 0.55, 0.56, 0.57, 0.58, 0.59, 0.60, 0.61, 0.62, 0.63, 0.64, 0.65, 0.66, 0.67, 0.68, 0.69, 0.70, 0.71, 0.72, 0.73, 0.74, 0.75, 0.76, 0.77, 0.78, 0.79, or 0.80, including any intervening range (e.g., 0.35-0.60).

In various embodiments, the methanogenesis stage is controlled such that the FOS/TAC ratio is about, at least about, or at most about 0.30, 0.31, 0.32, 0.33, 0.34, 0.35, 0.36, 0.37, 0.38, 0.39, 0.40, 0.41, 0.42, 0.43, 0.44, 0.45, 0.46, 0.47, 0.48, 0.49, 0.50, 0.51, 0.52, 0.53, 0.54, 0.55, 0.56, 0.57, 0.58, 0.59, 0.60, 0.61, 0.62, 0.63, 0.64, 0.65, 0.66, 0.67, 0.68, 0.69, 0.70, 0.71, 0.72, 0.73, 0.74, 0.75, 0.76, 0.77, 0.78, 0.79, or 0.80, including any intervening range (e.g., 0.37-0.50).

There are many types of monitoring for gas composition. For example, a low methane volume output from the methanogenesis stage indicates that the methanogenesis stage is "spent" and can be partially emptied, transferred, and filled in with fresh animal manure in the hydrolysis stage. In some embodiments, if compared to the highest volume of biogas generated in one day since the last fill, once daily biogas volume is about 25% of that number, then stage transfer should be completed and the hydrolysis stage filled with animal manure. For example, if after filling, the daily gas volume reaches 10 L per day then steadily starts dropping, the fill should be done at 2.5 L of gas generated in one day. One skilled in the art can conduct experiments to find the economic sweet spot for time versus methane generated.

In some embodiments, step (f) includes monitoring concentration of $H_2S$ to indicate a transition from hydrolysis to acidogenesis. Hydrogen sulfide ($H_2S$) can be an indicator for determining accurate stage isolation—that the organisms in a given stage have become and are continuing to be dominant in its correctly curated stage in the process. $H_2S$ is generated by acidogenic bacteria. Essentially, an increase in $H_2S$ trend indicates a transition from hydrolysis to acidogenesis. A stable plateau of $H_2S$ levels indicates ongoing acidogenesis. A sharp drop in $H_2S$ trend indicates a transition from acidogenesis to methanogenesis. Thus, in hydrolysis, at the first sign of $H_2S$ levels beginning to stabilize at a high range, a transfer to acidogenesis may be performed, as well as filling the hydrolysis stage. Once acidogenesis shows signs of dropping from its stable higher numbers, a transfer to methanogenesis is performed. Emptying the methanogenesis stage is then determined by gas output.

In some embodiments, the biogas produced in step (g) has a biomethane yield of at least 80%, wherein the biomethane yield is calculated as the ratio, expressed as a percentage, of the biomethane in the product divided by total biomethane potential associated with the feedstock (known as the biomethane potential, BMP). In certain embodiments, the biomethane yield is at least 85%, at least 90%, or at least 95%. The BMP represents how much methane can be extracted from a given feedstock. There are two reasons this metric is important: methane that is not extracted during digestion will likely be emitted into the atmosphere; and methane extracted in a digester is the primary revenue driver for the system. A lower BMP means more emissions from a feedstock and less revenue produced. In various embodiments, the biomethane yield is about, or at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

A typical composition of the gas product (prior to purification) is about 62 vol % $CH_4$, about 35 vol % $CO_2$, about 2.7 vol % $N_2$, and about 0.3 vol % $H_2S$. In various embodiments, the composition of the gas product (prior to purification) is from about 50 vol % to about 75 vol % $CH_4$, from about 30 vol % to about 40 vol % $CO_2$, from about 1 vol % to about 5 vol % $N_2$, and from about 0.01 vol % to about 0.5 vol % $H_2S$.

In some embodiments, the total residence time is about 30 days or less, wherein the total residence time is defined as the sum of the hydrolysis-stage residence time, the acidogenesis-stage residence time, and the methanogenesis-stage residence time. In certain embodiments, the total residence time is about 15 days or less. In various embodiments, the total residence time is about, or at most about, 30, 29, 28, 27, 26, 25, 24, 23, 22, 21, 20, 19, 18, 17, 16, 15, 14, 13, 12, 11, or 10 days. In a specific embodiment reduced to practice, a 13-day total residence time coincided with a 95% biomethane yield over the course of a three-month test. The 95% biomethane yield was surprisingly high.

A total residence time of about 10-30 days is a significant improvement over known manure digesters, which conventionally take about 60-90 days to process feedstock into biogas. This long processing period means that a conventional system must be capable of holding 60-90 days of feedstock in an anaerobic bioreactor. Maintaining an anaerobic environment at high enough temperatures for processing conventionally involves very large infrastructure footprints on a farm. In some cases, a conventional anaerobic digestion facility on a farm is almost as large as the barn the animals are kept in. This is a major issue for three reasons: many farms do not have enough space next to their barns without compromising productive land; these facilities take a very long time to build; and these large projects often do not produce enough revenue to be financially viable.

The biogas product is preferably upgraded by purifying it for the final use, such as pipeline-quality methane gas. Any known gas purification system may be employed to remove impurities and generate a relatively pure $CH_4$ stream and a relatively pure $CO_2$ stream. The relatively pure $CH_4$ stream may be at least 85 vol % $CH_4$, at least 90 vol % $CH_4$, at least 95 vol % $CH_4$, or at least 99 vol % $CH_4$, for example.

The biogas product need not be purified to produce pipeline-quality methane gas. Other potential uses of the biogas include direct combustion to generate electricity and/or heat, or steam reforming to generate syngas, for example. After being purified to generate a relatively pure $CH_4$ stream and a relatively pure $CO_2$ stream, the $CH_4$ stream also need not be used as a pipeline-quality methane gas. The $CH_4$ stream may alternatively (or additionally) be used to generate electricity and/or heat via combustion, or to generate syngas via steam reforming, partial oxidation, or autothermal reforming, for example. The syngas may then be further processed into a wide variety of chemicals or fuels, such as hydrogen, ammonia, alcohols, Fischer-Tropsch liquids, and so on.

In some embodiments, a single gas bladder is configured to collect gas from the methanogenesis stage. A "gas bladder" may be a fixed or portable container configured to receive and store biogas. Preferably, the gas bladder is constructed from a material, such as an elastic polymer, that can volumetrically expand as the bladder is filled with biogas. The gas bladder is preferably connected to a gas-purification system for purifying the biogas. Purified biomethane may be fed to another bladder or container (e.g., a mobile storage tank) for storing the biomethane, such as until the biomethane will be fed to a natural-gas pipeline. In certain embodiments, purified biomethane is fed directly into a natural-gas pipeline when it is situated in close proximity to the gas bladder.

FIG. 1 is an exemplary block-flow process diagram of a multi-stage process for anaerobic digestion of animal manure. In FIG. 1, which is non-limiting, animal manure is fed to a hydrolysis stage, an acidogenesis stage, and a methanogenesis stage during start-up. Each stage is equipped with a reaction monitor for monitoring the gas composition and/or the FOS/TAC ratio. Multiple reaction monitors may be used for any reaction stage. At a selected time based on reaction monitoring, animal manure is fed only to the hydrolysis stage; then the system is operated at steady state to generate biogas that is collected (e.g., in a gas bladder).

In FIG. 1, the biogas product exiting the methanogenesis stage is typically collected into a gas bladder as described above. In certain embodiments, gas is collected from the hydrolysis stage and the acidogenesis stage using a gas bladder that is distinct from a gas bladder collecting gas from the methanogenesis stage. In certain embodiments, the gas from the first two stages (hydrolysis and acidogenesis) may be bubbled to the third (methanogenesis) stage to increase its methane content.

As shown in FIG. 1, there is also usually a digestate co-product generated from the process and recovered from the methanogenesis stage. The digestate co-product is nutrient-rich material remaining after the animal manure undergoes anaerobic digestion to produce biogas. The digestate co-product can be used as a fertilizer or soil amendment to improve soil health, increase water retention, and reduce the need for chemical fertilizers. The digestate co-product can be separated into liquid and solid components, which can then be processed into various products such as compost, fertilizer pellets, livestock bedding, or bio-based building materials, for example.

Other variations provide a multi-stage anaerobic digester for anaerobic digestion of animal manure, wherein the multi-stage anaerobic digester comprises:

a digester input;

a hydrolysis stage connected to the digester input;

an acidogenesis stage connected to the hydrolysis stage, wherein the acidogenesis stage is physically separate from the hydrolysis stage;

a methanogenesis stage connected to the acidogenesis stage, wherein the methanogenesis stage is physically separate from the acidogenesis stage; and a digester output configured to recover a product comprising biogas, wherein each of the hydrolysis stage, the acidogenesis stage, and the methanogenesis stage is capable of forming an anaerobic environment, and wherein each of the hydrolysis stage, the acidogenesis stage, and the methanogenesis stage is configured with a first monitor and a second monitor, wherein the first monitor is configured for monitoring the gas composition, and wherein the second monitor is configured for monitoring the ratio of volatile fatty acids to total alkalinity.

The digester input may be configured to receive a feedstock comprising animal manure in liquid form dissolved in water and/or slurry form suspended in water. Alternatively, or additionally, the digester input may be configured to receive a feedstock comprising solid biomass and/or liquid biomass.

The multi-stage anaerobic digester may have three stages, or more than three stages. When there is an additional stage besides the primary hydrolysis stage, the primary acidogenesis stage, and the primary methanogenesis stage, the additional stage may be a secondary hydrolysis stage, a secondary acidogenesis stage, a secondary methanogenesis stage, an acetogenesis stage, a holding (non-reactive) stage, a gas-recovery stage, a gas-monitoring stage, or a combination thereof, for example.

In some embodiments, the multi-stage anaerobic digester is modular. As explained elsewhere, the disclosed three-stage digestion process enables the processing of feedstock into biogas in as fast as about 10 days. This results in much smaller digester volume requirements to process the same amount of feedstock when compared to current technology. Additionally, the disclosed three-stage digestion process can achieve a biomethane yield of at least 90% of biomethane potential. These process performance improvements enable a modular system. The modular system does not require the large infrastructure footprint of current technology and makes it economically viable to have feedstocks from many farms being processed in one centralized facility. The modular nature of the system also enables most fabrication to occur in a single manufacturing facility, which reduces planning costs and enables year-round construction. Modules may be delivered to a processing facility site for simple installation. The processing speed, gas yield, and system modularity results in a scalable technology capable of penetrating the entire hog and dairy commercial farming industries.

In some embodiments, the multi-stage anaerobic digester is automated via an automation sub-system. The automation sub-system typically includes a computer in wired or wireless communication with the multi-stage anaerobic digester, enabling process control. The automation sub-system may be configured to control flow rates, temperatures, processing times, gas compositions, FOS/TAC ratios, and other parameters in each stage.

In some embodiments, the multi-stage anaerobic digester utilizes a single pump for multiple stages. Some embodiments employ a novel pumping loop as follows. Instead of dedicating a pump to each process stage, all tank fill ports may be connected to a common pipe and all tank drain ports connected to a common pipe. Pumps (e.g., pump 408 or pump 409 in FIG. 4 discussed below) plumbed to the same common two lines can now complete any process by simply opening the corresponding valve. To avoid cross-contamination between stages and disrupt the distinct colonies in each stage, it is preferred to utilize a combination of clearing lines with compressed air from the system's stored gas, and limiting fluid volume left in the fluid lines.

In typical embodiments, the digester output is connected to one or more biogas bladders. The biogas bladder(s) may be connected to a methane purification system, which may be at the same site as the multi-stage anaerobic digester, or at another site, such as a gas purification site or a pipeline injection site.

In some embodiments, the first monitor is configured for monitoring concentration of $H_2S$ to indicate a transition from hydrolysis to acidogenesis. In various embodiments, the $H_2S$ concentration that indicates a transition from hydrolysis to acidogenesis is about 0.1 vol %, 0.2 vol %, 0.3 vol %, 0.4 vol %, 0.5 vol %, 0.6 vol %, 0.7 vol %, 0.8 vol %, 0.9 vol %, or 1 vol %, for example. The specific $H_2S$ concentration that indicates a transition from hydrolysis to acidogenesis will depend, at least in part, on the total sulfur content of the starting animal manure.

In some embodiments, the multi-stage anaerobic digester is configured to achieve a total residence time of about 30 days or less, such as about 15 days or less. In various embodiments, the multi-stage anaerobic digester is configured to achieve a total residence time of about, or less than about, 30, 29, 28, 27, 26, 25, 24, 23, 22, 21, 20, 19, 18, 17, 16, 15, 14, 13, 12, 11, or 10 days.

In some embodiments, the animal manure is swine manure. During operation, the animal manure is contained within the multi-stage anaerobic digester, undergoing conversion to biogas. After fabrication but prior to operation, there is typically no animal manure (or other feedstock) contained within the multi-stage anaerobic digester.

In some embodiments, the system is made up of (at least) three bioreactor tanks, one pump, valves, plumbing between reactors, pH and temperature probes in each tank, two gas bladders, and all necessary wiring and electronics for controlling and monitoring the system. In certain embodiments, the system includes a novel plumbing loop that enables use of a single pump to run the entire system. This results in a significantly lower capital cost compared to systems which need to process similar volumes of feedstock. The system is preferably automated to maintain the steady-state environment.

Figure 2A:
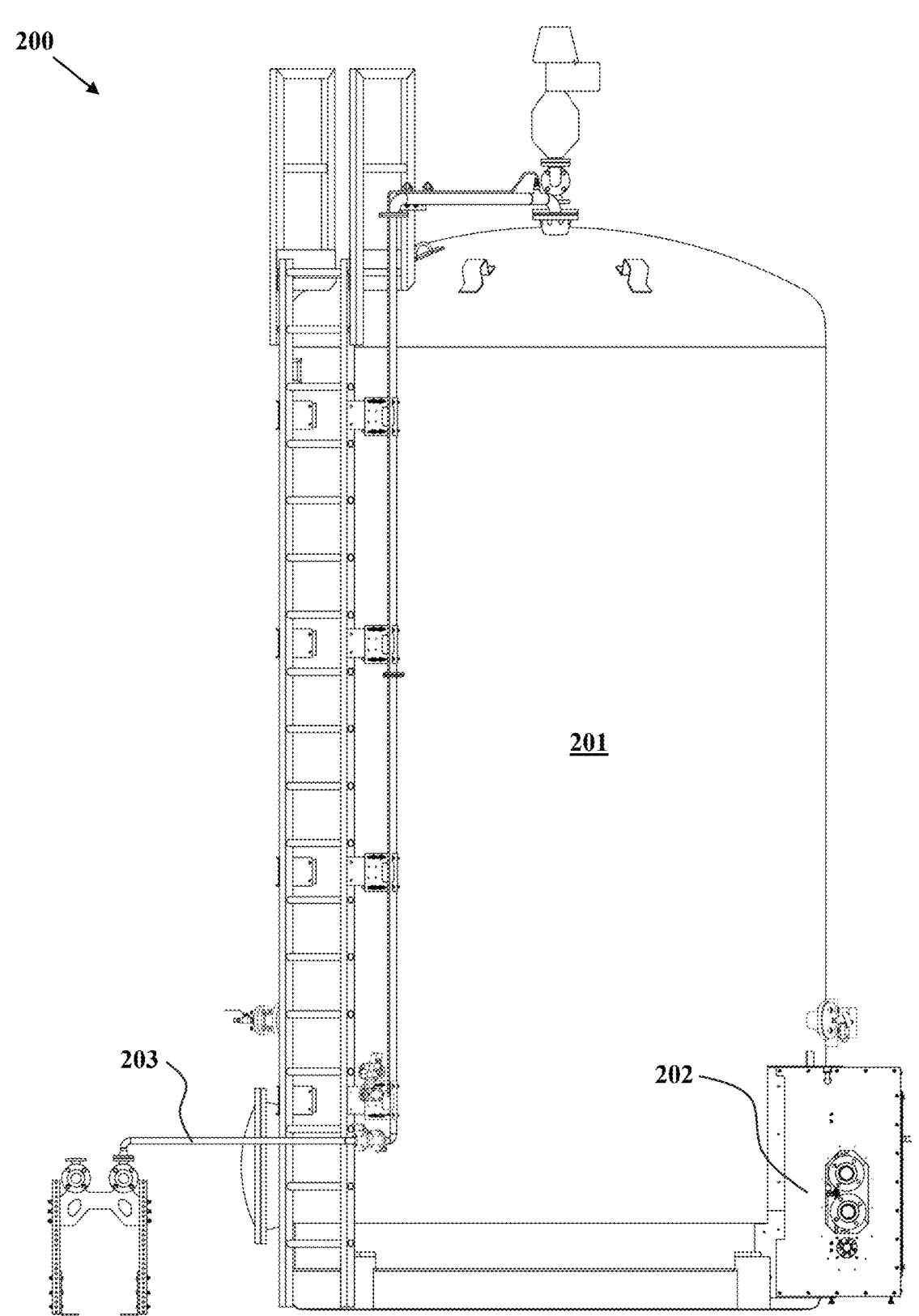
FIG. 2A (side view) depicts a tank assembly for use as the hydrolysis stage, the acidogenesis stage, or the methanogenesis stage, in various embodiments.
Figure 2B:
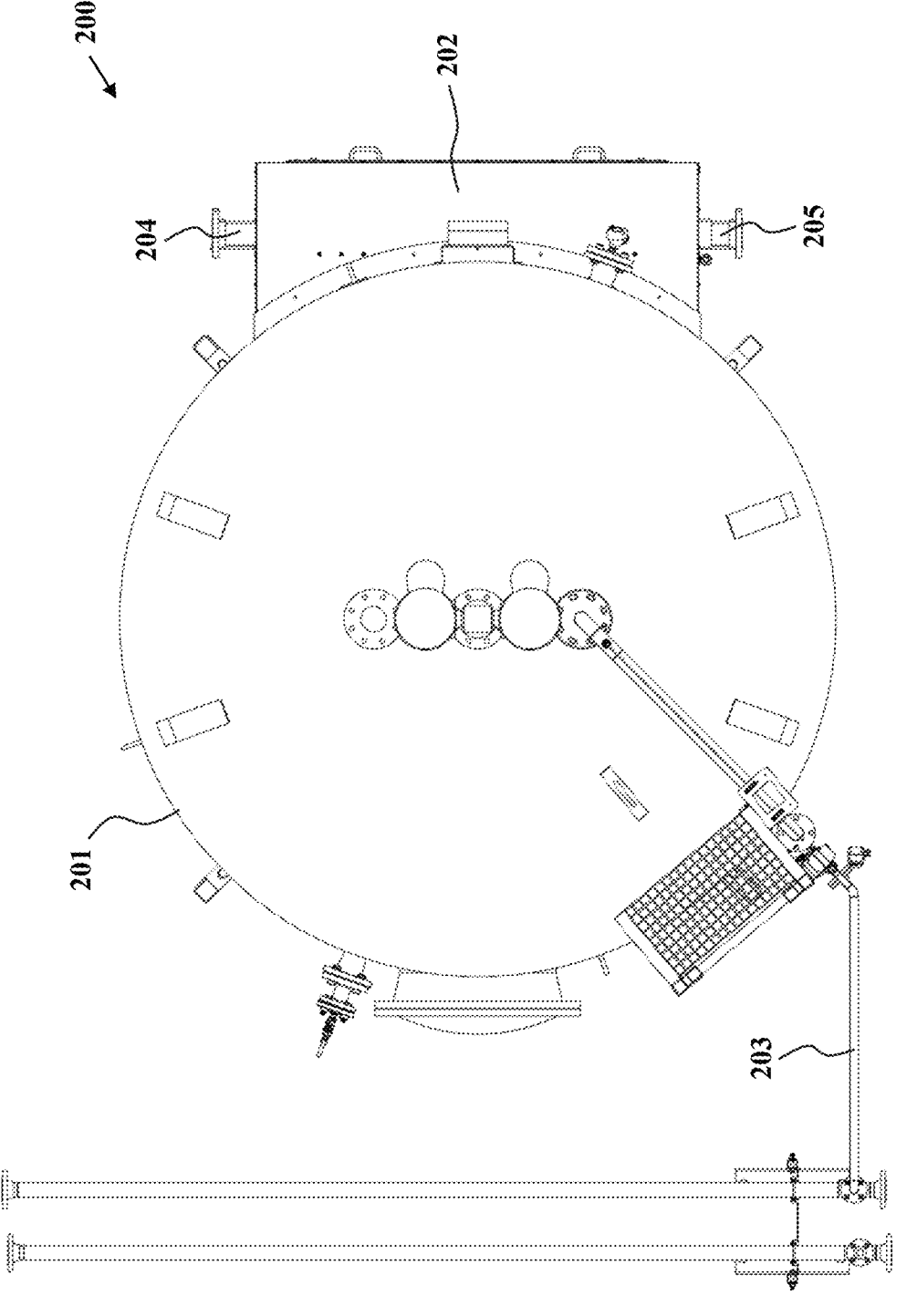
FIG. 2B (top view) depicts a tank assembly for use as the hydrolysis stage, the acidogenesis stage, or the methanogenesis stage, in various embodiments.

FIG. 2A (side view) depicts a tank assembly 200 for use as the hydrolysis stage, the acidogenesis stage, or the methanogenesis stage. The tank assembly 200 includes an insulated tank 201, a manure and digestate control sub-system 202, and a digester output 203 (gas collection line). FIG. 2B is a top view of FIG. 2A. FIG. 2B depicts a tank assembly 200 for use as the hydrolysis stage, the acidogenesis stage, or the methanogenesis stage. The tank assembly 200 includes an insulated tank 201, a manure and digestate control sub-system 202, and a digester output 203 (gas collection line). The digestate control sub-system 202 includes an inlet port 204 and an outlet port 205. When the tank assembly 200 is the hydrolysis stage, during operation, manure is fed into the inlet port 204, and hydrolyzed solids are removed from the outlet port 205. When the tank assembly 200 is the acidogenesis stage, during steady-state operation, hydrolyzed solids are fed into the inlet port 204, and an intermediate digestate is removed from the outlet port 205. During start-up, manure is fed into the inlet port 204 of the acidogenesis stage. When the tank assembly 200 is the methanogenesis stage, during steady-state operation, the intermediate digestate is fed into the inlet port 204, and a final digestate is removed from the outlet port 205. During start-up, manure is fed into the inlet port 204 of the methanogenesis stage.

Figure 3:
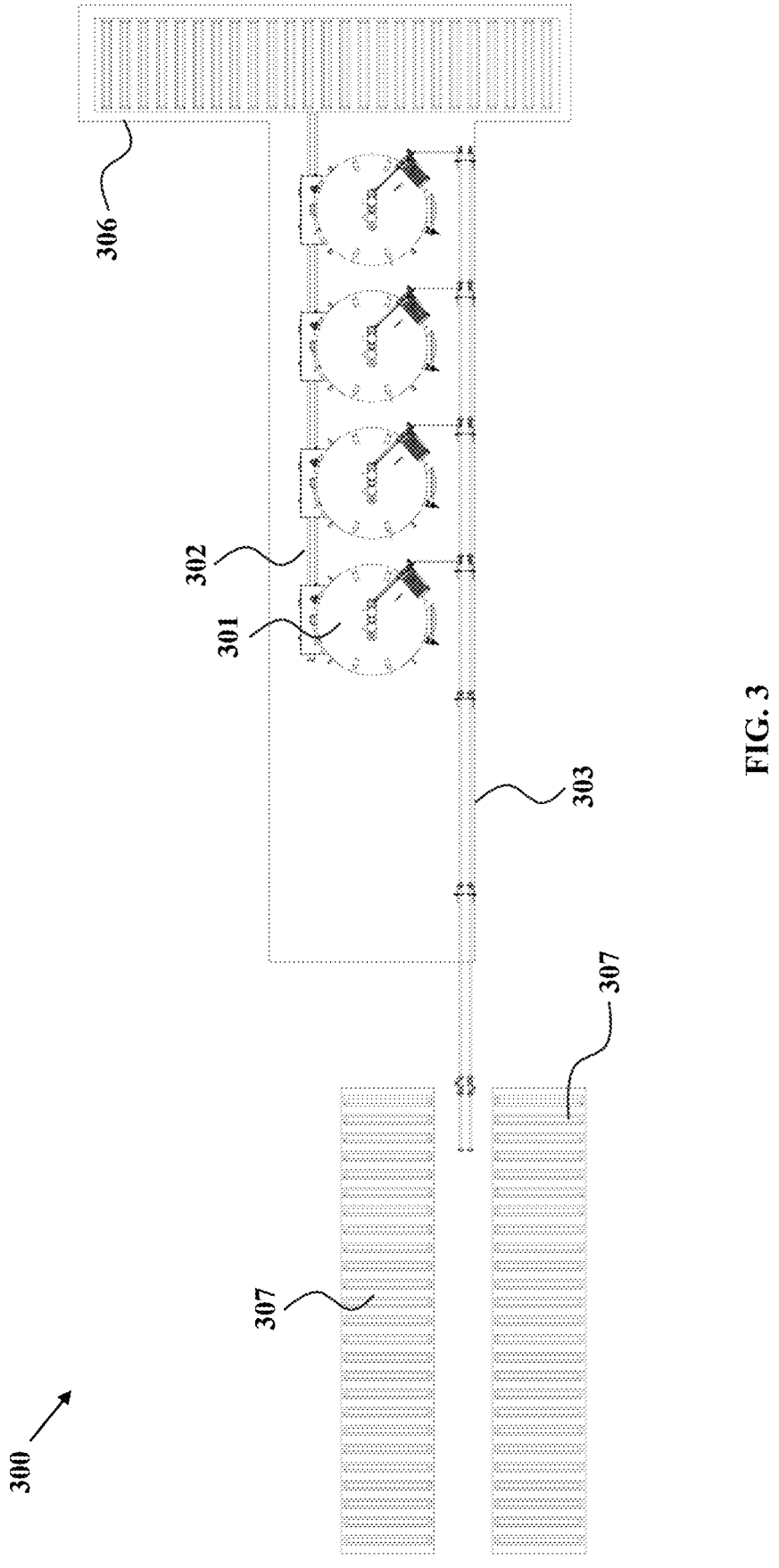
FIG. 3 (plan view) depicts an exemplary site assembly for a multi-stage anaerobic digester configured for anaerobic digestion of animal manure.

FIG. 3 (plan view) depicts an exemplary site assembly 300 for a multi-stage anaerobic digester configured for anaerobic digestion of animal manure. The site assembly 300 includes a plurality of digester tank assemblies 301, manure/digestate lines 302, gas collection lines 303, a pump house 306, and biogas storage 307.

Figure 4:
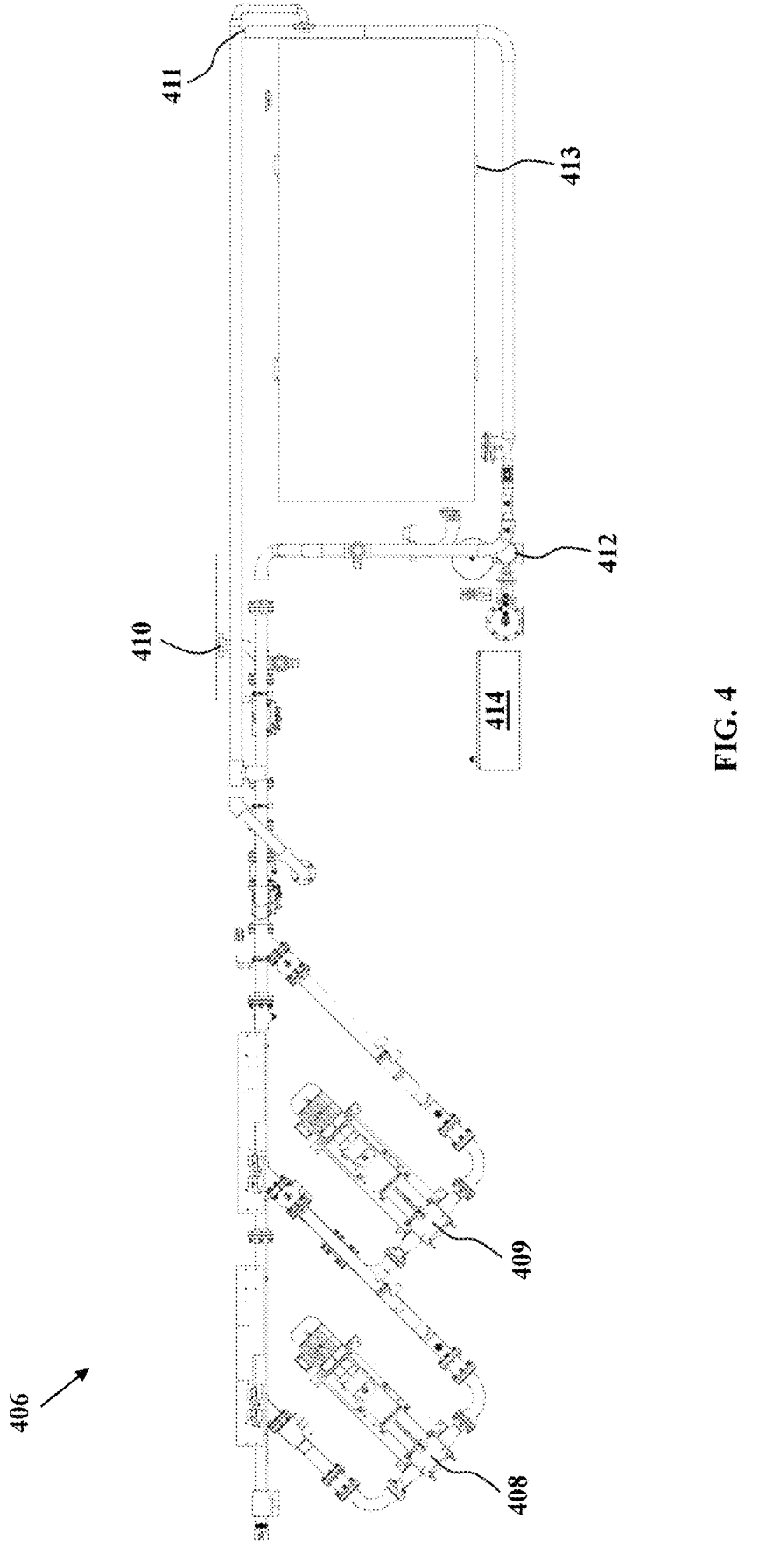
FIG. 4 depicts an exemplary pump house configured with a first mainline pump, a second mainline pump, a connection to the tank farm, a connection to the barn, hot-water recirculation, a heat exchanger, and an electrical sub-system.

FIG. 4 depicts an exemplary pump house 406. The pump house 406 is configured with a first mainline pump 408, a second mainline pump 409, a connection to the tank farm 410, a connection to the barn 411, hot-water recirculation 412, a heat exchanger 413, and an electrical sub-system 414. The connection to the tank farm 410 is the same as the connection shown in FIG. 3 between the pump house 306 and the manure/digestate lines 302 that connect to the digester tank assembly 301 adjacent to the pump house 306. The connection to the tank farm 410 consists of one common fill line and one common drain line that can service any tank. The connection to the barn 411 also consists of one system fill line and one system drain line. The pump house 406 contains selector valves between the pumps and the rest of the pump house. Pump 408 and/or 409 can be switched from pumping from/to the barn 411 or from/to the tank farm 410 by selecting which selector valves are opened within the pump house 406. Operations that only require one pump can be performed using either pump 408 or 409.

As will be appreciated by a skilled engineer, the processes and systems of the invention may employ various process sensors and control schemes to monitor and control gas pressures, temperatures, flow rates, and compositions throughout processing. Standard or customized gas pressure, temperature, and flow gauges may be employed. Gas composition may be monitored by withdrawing a gas sample and subjecting the gas sample to mass spectrometry, gas chromatography, or FTIR spectroscopy, for example. Gas composition may be measured, for example, according to ASTM D7833, D1945, D1946, or D3588, which test methods are incorporated by reference herein. Process adjustments may be made dynamically using measurements of gas compositions, flow rates, temperatures, etc., if deemed necessary or desirable, using well-known principles of process control (feedback, feedforward, proportional-integral-derivative logic, etc.).

As will also be appreciated by a skilled artisan, the processes and systems of the invention may utilize various process simulations, modeling, and engineering calculations, both in the initial design as well as during operation. Process calculations and simulations may be performed using process simulation software (e.g., Aspen Plus).

Conventionally, capital cost is closely tied to slow processing speed because slow speeds increase the volume storage requirements for the digester. Many farmers lack excess unused space on their farm and most farms have different layouts from each other. This means that most agricultural digesters require bespoke design elements for each project, which increases the planning costs for a project. The size of the digester often requires a full-scale construction project from building the foundation for the digester to erecting the structure itself. This takes many different types of engineers and is very costly labor. There is also an opportunity cost: these projects take a very long time to build, sometimes up to two years. A major constraint that impacts building time is that during wintertime, much of this work cannot be done due to the inclement weather. This long time to build is time while waste emissions are escaping into the atmosphere and methane is not being captured to be sold.

In some embodiments of the disclosed technology, individual farms are equipped with a multi-stage anaerobic digester. In some embodiments, a centralized digestion facility is configured with a multi-stage anaerobic digester, wherein the centralized digestion facility receives animal manure from multiple farms for central processing into biogas. In some embodiments, biogas product is collected from multiple farms for purification at a centralized purification facility. A centralized purification facility may be at the same site as a centralized digestion facility, but that is not necessary. Within a certain region (e.g., the Midwest United States), there may be multiple centralized facilities.

The disclosed multi-stage process for anaerobic digestion is a carbon net-neutral or net-negative process that harnesses the power of methane released by waste. By avoiding methane release to the atmosphere, the greenhouse-gas impact of animal manure is significantly improved. This benefit arises because animal manure generates a lot of methane, a potent greenhouse gas (over an order of magnitude worse than carbon dioxide), as the manure decomposes anaerobically. Anaerobic environments are common especially in large manure storage systems like lagoons, where bacteria break down organic matter in the absence of air, producing methane and carbon dioxide. For that reason, animal manure is ordinarily a significant source of agricultural methane emissions.

The disclosed invention flips the script, capturing usable methane rather than allowing its uncontrolled release to the Earth's atmosphere. When the methane is later combusted and generates carbon dioxide that is emitted to the atmosphere, that $CO_2$ is renewable because it originated from agriculture—e.g., corn or soybeans grown using photosynthesis, followed by animal digestion of corn and soybean meal to make animal manure. The circular $CO_2$ does not cause a net contribution to greenhouse gases. The biogas produced may receive a renewable natural gas credit. The renewable natural gas credit may be provided by the operator of the natural gas pipeline, a government agency that regulates the natural gas pipeline, a non-governmental organization that advocates for renewal fuels, and/or another entity.

In this detailed description, reference has been made to multiple embodiments and to the accompanying drawing(s) in which are shown by way of illustration specific exemplary embodiments of the invention. These embodiments are described in sufficient detail to enable those skilled in the art to practice the invention, and it is to be understood that modifications to the various disclosed embodiments may be made by a skilled artisan.

Where methods and steps described above indicate certain events occurring in certain order, those of ordinary skill in the art will recognize that the ordering of certain steps may be modified and that such modifications are in accordance with the variations of the invention. Additionally, certain steps may be performed concurrently in a parallel process when possible, as well as performed sequentially.

All publications, patents, and patent applications cited in this specification are herein incorporated by reference in their entirety as if each publication, patent, or patent application were specifically and individually put forth herein.

The embodiments, variations, and drawings described above should provide an indication of the utility and versatility of the present invention. Other embodiments that do not provide all of the features and advantages set forth herein may also be utilized, without departing from the spirit and scope of the present invention. Such modifications and variations are considered to be within the scope of the invention defined by the claims.

What is claimed is:

1. A multi-stage process for anaerobic digestion of animal manure, wherein said multi-stage process comprises:
    (a) providing a feedstock comprising animal manure, wherein said animal manure is in liquid form dissolved in water and/or slurry form suspended in water;
    (b) introducing a first start-up amount of said feedstock and a hydrolytic microorganism to a hydrolysis stage, wherein said first start-up amount of said feedstock and said hydrolytic microorganism are introduced batch-wise, wherein said hydrolytic microorganism is contained with said first start-up amount of said feedstock, and wherein said hydrolysis stage is operated in step (g) at a hydrolysis temperature selected from about 50° C. to about 65° C.;
    (c) introducing a second start-up amount of said feedstock and an acidogenic microorganism to an acidogenesis stage, wherein said second start-up amount of said feedstock and said acidogenic microorganism are introduced batchwise, wherein said acidogenic microorganism is contained with said second start-up amount of said feedstock, and wherein said acidogenesis stage is operated in step (g) at an acidogenesis temperature selected from about 50° C. to about 70° C.;
    (d) introducing a third start-up amount of said feedstock and a methanogenic microorganism to a methanogenesis stage, wherein said third start-up amount of said feedstock and said methanogenic microorganism are introduced batchwise, wherein said methanogenic microorganism is contained with said third start-up amount of said feedstock, wherein said methanogenesis stage is operated in step (g) at a methanogenesis temperature selected from about 50° C. to about 75° C.;
    (e) forming an anaerobic environment in each of said hydrolysis stage, said acidogenesis stage, and said methanogenesis stage;

(f) monitoring gas composition and ratio of volatile fatty acids to total alkalinity in each of said hydrolysis stage, said acidogenesis stage, and said methanogenesis stage; and
    (g) feeding a steady-state amount of said feedstock into said hydrolysis stage, and processing said steady-state amount of said feedstock, continuously or intermittently, through said hydrolysis stage, said acidogenesis stage, and said methanogenesis stage, thereby generating a product comprising biogas, wherein step (g) is triggered based on both monitored gas composition obtained during step (f), and monitored ratio of said volatile fatty acids to said total alkalinity obtained during step (f).

2. The multi-stage process of claim 1, wherein said animal manure is swine manure.

3. The multi-stage process of claim 1, wherein said hydrolytic microorganism has a genus selected from the group consisting of *Coprothermobacter, Acetomicrobium*, and *Thermoanaerobacterium*.

4. The multi-stage process of claim 1, wherein said hydrolysis stage is operated in step (g) at a hydrolysis-stage residence time selected from about 1 day to about 5 days.

5. The multi-stage process of claim 1, wherein said acidogenic microorganism has a genus selected from the group consisting of *Acetitomaculum, Acetoanaerobium, Acetonema, Anaerovorax*, Candidatus Phosphitivorax, Dehalobacterium, *Moorella*, Romboutsia, *Ruminococcus*, and Terrisporobacter.

6. The multi-stage process of claim 1, wherein said acidogenesis stage is operated in step (g) at an acidogenesis-stage residence time selected from about 5 days to about 14 days.

7. The multi-stage process of claim 1, wherein said methanogenic microorganism has a genus selected from the group consisting of *Methanobacterium, Methanoculleus, Methanothermobacter, Methanosarcina, Methanothrix*, and *Methanospirillum*.

8. The multi-stage process of claim 1, wherein said methanogenesis stage is operated in step (g) at a methanogenesis-stage residence time selected from about 7 days to about 14 days.

9. The multi-stage process of claim 1, wherein total residence time is about 30 days or less, wherein said total residence time is defined as the sum of hydrolysis-stage residence time, acidogenesis-stage residence time, and methanogenesis-stage residence time.

10. The multi-stage process of claim 9, wherein said total residence time is about 15 days or less.

11. The multi-stage process of claim 1, wherein step (f) includes monitoring concentration of $H_2S$ to indicate a transition from hydrolysis to acidogenesis.

12. The multi-stage process of claim 1, wherein said biogas produced in step (g) has a biomethane yield of at least 80%, wherein said biomethane yield is calculated as a ratio, expressed as a percentage, of biomethane in said product divided by total biomethane potential associated with said feedstock.

13. The multi-stage process of claim 12, wherein said biomethane yield is at least 85%.

14. The multi-stage process of claim 12, wherein said biomethane yield is at least 90%.

* * * * *